United States Patent
Butler

[11] Patent Number: 5,356,905
[45] Date of Patent: Oct. 18, 1994

[54] NEUROPROTECTIVE 3-PIPERIDINO-4-HYDROXYCHROMAN DERIVATIVES AND ANALOGS

[75] Inventor: Todd W. Butler, New London, Conn.

[73] Assignee: Pfizer Inc., New York, N.Y.

[21] Appl. No.: 916,130

[22] PCT Filed: Feb. 6, 1990

[86] PCT No.: PCT/US90/00674
§ 371 Date: Jul. 23, 1992
§ 102(e) Date: Jul. 23, 1992

[87] PCT Pub. No.: WO91/12005
PCT Pub. Date: Aug. 22, 1991

[51] Int. Cl.$^5$ ............... A61K 31/445; C07D 211/14; C07D 405/04
[52] U.S. Cl. ...................... 514/320; 514/304; 514/319; 546/124; 546/126; 546/128; 546/196; 546/206
[58] Field of Search ............... 514/299, 319, 320, 304; 546/112, 196, 206, 124, 126, 128

[56] References Cited

U.S. PATENT DOCUMENTS

| | | | |
|---|---|---|---|
| 3,294,804 | 12/1966 | Carabateas | 260/294.3 |
| 3,509,164 | 4/1979 | Carron et al. | 260/294.7 |
| 4,016,281 | 4/1977 | Jonas et al. | 424/267 |
| 4,048,317 | 9/1977 | Watts | 544/150 X |
| 4,446,113 | 5/1984 | Evans et al. | 548/407 X |
| 4,610,992 | 9/1986 | Evans et al. | 514/320 |
| 4,640,928 | 2/1987 | Willcocks | 514/422 |

OTHER PUBLICATIONS

Chemical Abstracts 89, (43498) 1978.
Chemical Abstracts 89, (146938w) 1978.
Carter, et al., J. Pharmacology & Experimental Therapeutics 247, 1222 (1988).
Gotti, et al., J. Pharmacology & Experimental Therapeutics 247, 1211 (1988).

*Primary Examiner*—Robert W. Ramsuer
*Assistant Examiner*—Jacqueline Haley
*Attorney, Agent, or Firm*—Peter C. Richardson; Gregg C. Benson; Mervin E. Brokke

[57] ABSTRACT

3-Piperidino-1-chromanol derivatives and analogs having the formula

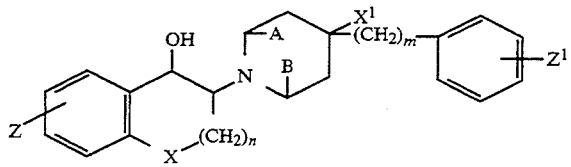

wherein
A and B are taken together and are —CH$_2$CH$_2$— or A and B are taken separately and are each H;
X is CH$_2$ or O;
X$^1$ is H or OH;
Z is H, F, Cl, Br or OH;
Z$^1$ is H, F, Cl, Br or (C$_1$-C$_3$)alkyl;
n is 0 or 1; and
m is 0 or an integer from 1 to 6;

pharmaceutical compositions thereof; methods of treating CNS disorders therewith; and intermediates useful in the preparation of said compounds.

17 Claims, No Drawings

NEUROPROTECTIVE 3-PIPERIDINO-4-HYDROXYCHROMAN DERIVATIVES AND ANALOGS

BACKGROUND OF THE INVENTION

The present invention is directed to neuroprotective (antiischemic and excitory aminoacid receptor blocking) 3-piperidino-1-chromanol derivatives and analogs, defined by the formula (I), below; pharmaceutically acceptable salts thereof; a method of using these compounds in the treatment of stroke or CNS degenerative diseases such as Alzheimer's disease, Huntington's disease and Parkinson's disease; and to certain intermediates therefor.

Ifenprodil is a racemic, so-called dl-erythro compound having the relative stereochemical formula

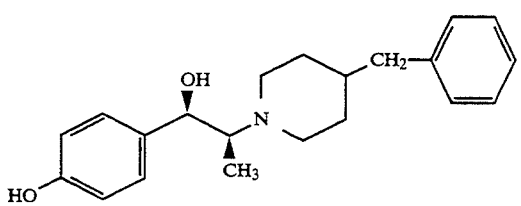

which is marketed as a hypotensive agent, a utility shared by a number of close analogs; Carron et al., U.S. Pat. No. 3,509,164; Carron et al., Drug Res., v. 21, pp. 1992-1999 (1971). More recently, ifenprodil has been shown to possess antiischemic and excitory aminoacid receptor blocking activity; Gotti et al., J. Pharm. Exp. Therap., v. 247, pp. 1211-21 (1988); Carter et al., loc. cit., pp. 1222-32 (1988). See also published European patent application 322,361 and French Patent 2546166. A goal, substantially met by the present invention, has been to find compounds possessing such neuroprotective effect in good measure, while at the same time having lowered or no significant hypotensive effect.

Certain structurally related 1-phenyl-3-(4-aryl-4-acyloxypiperidino)-1-propanols have also been reported to be useful as analgesics, U.S. Pat. No. 3,294,804; and 1-[4-(amino- and hydroxy-alkyl)phenyl]-2-(4-hydroxy-4-tolylpiperazino)-1-alkanols and alkanones have been reported to possess analgesic, antihypertensive, psychotropic or antiinflammatory activity, Japanese Kokai 53-02,474 (CA 89:43498y; Derwent Abs. 14858A) and 53-59,675 (CA 89:146938w; Derwent Abs. 48671A).

The nomenclature used herein is generally that of Rigaudy et al., IUPAC Nomenclature of Organic Chemistry, 1979 Edition, Pergammon Press, New York. Chromans are alternatively named as 3,4-dihydro-1(2H)-benzopyrans.

SUMMARY OF THE INVENTION

The present invention is directed to compounds of the formula

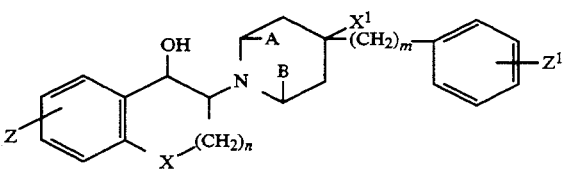

wherein
A and B are taken together and are —CH$_2$CH$_2$— or A and B are taken separately and are each H;
X is CH$_2$ or O;
X$^1$ is H or OH;
Z is H, F, Cl, Br or OH;
Z$^1$ is H, F, Cl, Br or (C$_1$-C$_3$)alkyl;
n is 0 or 1; and
m is 0 or an integer from 1 to 6; and to the pharmaceutically acceptable salts thereof.

For their ease of preparation and valuable biological activity, preferred compounds of the formula (I) have A and B taken separately (and so are each hydrogen ), Z is H, F, Cl or OH; Z$^1$ is H and m is 0, 1 or 2. When X is O and n is 1, the more preferred compounds have the cis relative stereochemical formula

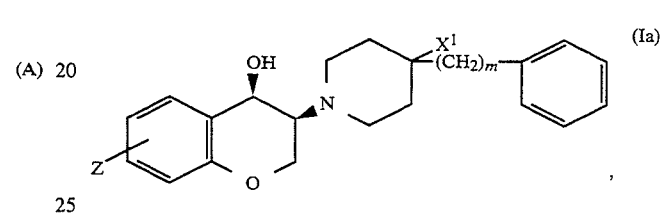

particularly those compounds wherein Z is OH and substituted at the 7-position of the chroman ring system. Most preferred compounds of the formula (Ia) are those wherein m is 0 or 2. When X is CH$_2$ and n is 1, the more preferred have the trans relative stereochemical formula

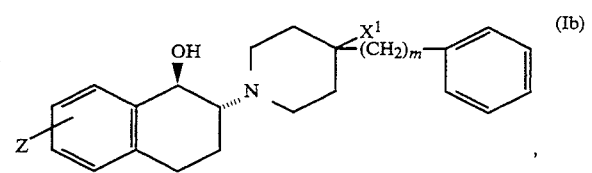

those compounds wherein Z is OH substituted at the 6-position of the 1,2,3,4-tetrahydronaphthalene ring system being of particular value. Most preferred compounds of the formula (Ib) are those wherein X$^1$ is OH and m is O. When n is 0, the more preferred compounds have X as CH$_2$, X$^1$ as OH, Z as OH substituted at the 5-position of the indane ring system and m as O.

The present invention is also directed to intermediate compounds of the formula

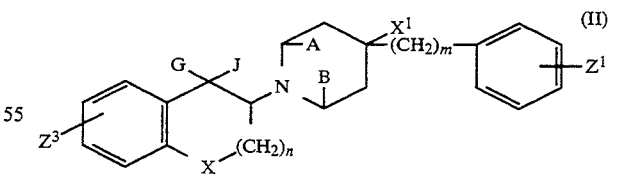

wherein
A and B, X, X$^1$, Z$^1$, m and n are as defined above;
G and J are taken together and are oxygen (forming a carbonyl group), or G and J are taken separately and G is H and J is hydroxy;
Z$^3$ is H, F, Cl, Br or OR;
R is H or a conventional hydroxy protecting group; with the proviso that when G and J are taken separately, Z$^3$ is OR$^1$ and R$^1$ is a conventional hydroxy protecting group;

and to intermediates of the formula

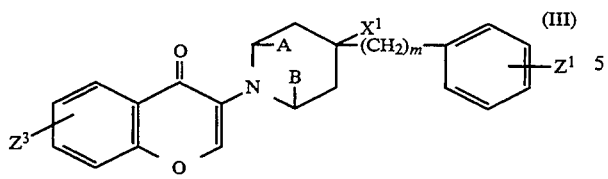

wherein the variable groups are as defined above.

The present invention is further directed to pharmaceutical compositions comprising a compound of the formula (I) and to a method of treating stroke or a CNS degenerative disease with a compound of the formula (I).

The above reference to "pharmaceutically acceptable salts" in all instant cases refers to conventional acid addition salts. Thus the compounds of the formula (I) contain an amine group which is basic, and so are capable of forming such salts. Said salts include, but are not limited to, those with HCl, HBr, HNO$_3$, H$_2$SO$_4$, H$_3$PO$_4$, CH$_3$SO$_3$H, p-CH$_3$C$_6$H$_4$SO$_3$H, CH$_3$CO$_2$H, gluconic acid, tartaric acid, maleic acid and succinic acid. They are generally prepared by conventional methods, e.g., by combining a compound of the formula (I) with at least one molar equivalent of the acid in a suitable solvent. Those compounds of the formula (I) which contain a phenolic hydroxy group are also capable of forming cationic salts (e.g., Na, K and the like); and the phrase "pharmaceutically acceptable salts" is also intended to encompass such salts. These salts, too, are prepared by conventional methods, e.g., by combining a phenolic compound of the formula (I) with one molar equivalent of NaOH or KOH in a suitable solvent.

DETAILED DESCRIPTION OF THE INVENTION

The pharmacologically active compounds of the present invention, having the formula (I) as noted above, are readily prepared.

When Z is OH in a compound of the formula (I), the immediate precursor will generally be a corresponding compound of the above formula (II) wherein G and H are taken separately, G is hydrogen, H is hydroxy, Z$^3$ is Or and R is conventional hydroxy protecting group. The protecting group is removed in the final step by conventional methods. The groups are preferably protected in the form of conventional silyl ethers, e.g., R is triisopropylsilyl or t-butyldimethylsilyl. The preferred method for removing such silyl groups employs 1 to 1.1 molar equivalents of tetrabutylammonium fluoride in a reaction inert solvent such as tetrahydrofuran, a reaction conveniently carried out at about 0°–50° C., most conveniently at ambient temperature so as to avoid the cost of heating or cooling the reaction mixture.

As used in the preceding paragraph, and elsewhere herein, the expression "reaction inert solvent" refers to any solvent which does not interact with starting materials, reagents, intermediates or products in a manner which adversely affects the yield of the desired product.

Compounds of the formula (I) wherein Z is other than OH, as well as intermediate compounds of the formula (II) wherein Z$^3$ is a protected hydroxy group, are generally prepared by conventional hydride reduction of an alpha-amino ketone, e.g.,

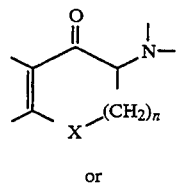

or

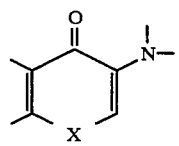

which in general produces a mixture of cis- and trans-isomers, e.g., respectively,

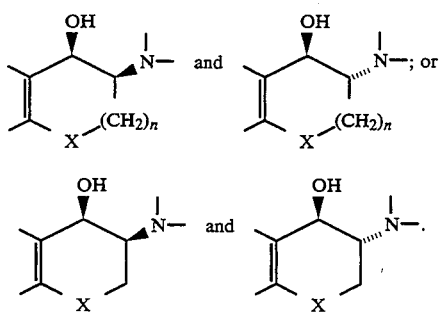

Of course, in individual cases, one or the other of these cis- or trans- isomers will frequently predominate.

These hydride reductions are carried out using conventional hydride reducing agents, e.g., NaBH$_4$ or LiAlH$_4$. The latter hydride reagent is usually used in excess (e.g., mol for mol), in a reaction inert solvent such as tetrahydrofuran, at reduced temperature (e.g., −15° C. to 15° C.). Alternatively, ketone intermediates, particularly those containing ester groups, are reduced with a milder hydride reducing agent such as NaBH$_4$, again usually in excess, now in a protic solvent such as methanol or ethanol, generally at somewhat higher temperature, e.g., 15°–45° C. Any protecting groups which are still in place after ketone reduction are then removed according to the methods described above.

Intermediate compounds of the type (A) as depicted above are generally prepared by reaction of a corresponding monobromo compound with a suitably substituted amine:

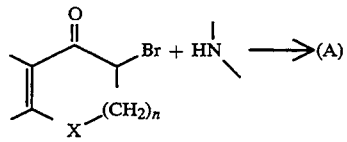

It will be obvious to those skilled in the art that the alpha-bromo group can be replaced by another nucleophilically displaceable group (e.g., C$_1$ or OSO$_2$CH$_3$). This reaction is carried out under conditions typical of nucleophilic displacements in general. Where the two reactants are about equivalent in availability, close to substantially molar equivalents may be used; although when one is more readily available, it is usually preferred to use that one in excess, in order to force this bimolecular reaction to completion in a shorter period of time. The reaction is generally carried out in the presence of at least 1 molar equivalent of a base, the piperidine derivative itself, if it is readily available, but more usually a tertiary amine which is at least comparable in base strength to the nucleophilic piperidine; and in a reaction inert solvent such as ethanol. If desired, the reaction is catalyzed by the addition of up to one molar equivalent or more of an iodide salt (e.g., NaI, KI). Temperature is not critical, but will generally be somewhat elevated in order to force the reaction to completion within a shorter time period, but not so high as to lead to undue decomposition. A temperature in the range of 50°-120° C. is generally satisfactory. Conveniently, the temperature is the reflux temperature of the reaction mixture.

Intermediate compounds of the type (B) as depicted above are generally prepared by reaction of the corresponding alpha, alpha-dibromo compound with a suitably substituted amine, e.g.,

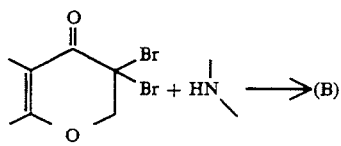

Except to use at least one additional molar equivalent of base (to neutralize the HBr formed in the concurrent dehydrohalogenation), conditions are analogous to those described above for the preparation of compounds of the type (A) by nucleophilic displacement.

The compounds of the formula (I) contain two asymmetric carbons—corresponding to two racemates and four optically active compounds. One of these racemates is the above noted cis-isomer, and the other the trans-isomer. Each of these racemates is capable of resolution into a pair of enantiomers via diastereomeric acid addition salts with an optically active acid. Alternatively, the racemic alcohol is converted to corresponding diastereomeric esters or urethanes formed with an optically active acid or isocyanate. Such covalently bonded derivatives are subjectable to a variety of separation methods (e.g., chromatography). Such diastereomeric esters are formed from the alcohol and the optically active acid by standard methods, generally those involving activation of the acid, e.g., as the acid chloride, as a mixed anhydride with an alkyl chloroformate, or with a dehydrative coupling agent such as dicyclohexylcarbodiimide. Once the resulting diastereomeric esters are separated, e.g., by chromatographic methods, they are hydrolyzed by conventional methods, e.g., aqueous acid or aqueous base, to obtain the enantiomeric, optically active alcohol compounds of the formula (I). It is the intent of applicant that this application not be limited to the racemic cis- and trans- compounds specifically exemplified below.

The starting materials and reagents required for the synthesis of the compounds of the present invention are readily available, either commercially, according to literature methods, or by methods exemplified in Preparations below.

The present compounds of the above formula (I) possess selective neuroprotective activity, based upon their antiischemic activity and ability to block excitatory aminoacid receptors, while at the same time having lowered or no significant hypotensive activity. The antiischemic activity of the present compounds is determined according to one or more of the methods which have been detailed previously by Gotti et al. and Carter et al. cited above, or by similar methods. The ability of the compounds of the present invention to block excitatory amino acid receptors is demonstrated by their ability to block N-methyl-D-aspartic acid-induced (NMDA) elevations of cGMP in neonatal rat cerebellums according to the following procedure. Cerebellums from ten 8-14 day old Wistar rats are quickly excised and placed in 4° C. Krebs/bicarbonate buffer, pH 7.4 and then chopped in 0.5 mm×0.5 mm sections using a McIlvain tissue chopper (The Nickle Laboratory Engineering Co., Gomshall, Surrey, England). The resulting pieces of cerebellum are transferred to 100 ml of Krebs/bicarbonate buffer at 37° C. which is continuously equilibrated with 95:5 $O_2/CO_2$. The pieces of cerebellum are incubated in such a manner for ninety minutes with three changes of the buffer. The buffer then is decanted, the tissue centrifuged (1 min., 3200 r.p.m.) and the tissue resuspended in 20 ml of the Krebs/bicarbonate buffer. Then, 250 µl aliquots (approximately 2 mg) are removed and placed in 1.5 ml microfuge tubes. To those tubes are added 10 µl of the compound under study from a stock solution followed, after a 10 minute incubation period, by 10 µl of a 2.5 mM solution of NMDA to start the reaction. The final NMDA concentration is 100 µM. Controls do not have NMDA added. The tubes are incubated for one minute at 37° C. in a shaking water bath and then 750 µl of a 0 mM Tris-Cl, 5 mM EDTA solution is added to stop the reaction. The tubes are placed immediately in a boiling water bath for five minutes. The contents of each tube then are sonicated for 15 seconds using a probe sonicator set at power level three. Ten microliters are removed and the protein determined by the method of Lowry, Anal. Biochem. 100: 201-220 (1979). The tubes are then centrifuged (5 min., 10,000 xg), 100 µl of the supernatant is removed and the level of cyclic GMP (cGMP) is assayed using a New England Nuclear (Boston, Massachusetts) cGMP RIA assay according to the method of the supplier. The data is reported as pmole cGMP generated per mg. protein. Undesired hypotensive activity is also determined by known methods, for example, according to the methods of Carron et al., also cited above.

Such selective neuroprotective antiischemic and excitatory amino acid blocking activities reflect the valuable utility of the present compounds in the treatment of degenerative CNS (central nervous system) disorders such as stroke; and Alzheimer's disease, Parkinson's disease and Huntington's disease; without significant potential for concurrent undue drop in blood pressure. In the systemic treatment of such diseases with a neuroprotective amount of compounds of the formula (I), the dosage is typically from about 0.02 to 10 mg/kg/day (1-500 mg/day in a typical human weighing 50 kg) in single or divided doses, regardless of the route of administration. Of course, depending upon the exact compound and the exact nature of the individual illness, doses outside this range may be prescribed by the attending physician. The oral route of administration is generally preferred. However, if the patient is unable to swallow, or oral absorption is otherwise impaired, the preferred route of administration will be parenteral (i.m., i.v.) or topical.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; and for topical administration, in the form of solutions, lotions, ointments, salves and the like.

The present invention is illustrated by the following examples, but is not limited to the details thereof.

All non-aqueous reactions were run under nitrogen for convenience and generally to maximize yields. All solvents/diluents were dried according to standard published procedures or purchased in a predried form. All reactions were stirred either magnetically or mechanically. NMR spectra are recorded at 300 MHz and are reported in ppm. The NMR solvent was $CDCl_3$ unless otherwise specified. IR spectra are reported in $cm^{-1}$, generally specifying only strong signals. The following abbreviations are used: DMF for dimethylformamide, THF for tetrahydrofuran, HRMS for high resolution mass spectrum.

EXAMPLE 1

3-(4-Hydroxy-4-phenylpiperidino)-7-(triisopropylsilyloxy)chromen-4-one 3,3-Dibromo-7-(triisopropylsilyloxy)-4-chromanone (5.0 g, 10.5 mmol) was dissolved in $CH_3CN$ (150 ml) and 4-hydroxy-4-phenylpiperidine (2.2 g, 12.5 mmol) and triethylamine (2.9 ml, 20.8 mmol) were added. The mixture was stirred overnight at ambient temperature, then concentrated and the residue partitioned between ethyl acetate and water. The organic layer was washed with water (2×50 ml) and brine, dried over $CaSO_4$, concentrated, and the residue chromatographed on silica gel, using gradient elution with ethyl acetate/hexane to yield title product as a white solid (2.3 g, 54%). A portion was recrystallized from ethanol/ether; mp 163°–163.5° C.; IR (KBr) 3437, 2950, 2870, 1635, 1615, 1600, 1447, 1285, 1247, 1200, 1185, 703, 690. Anal. Calcd. for $C_{29}H_{39}NO_4Si$: C, 70.55; H, 7.96; N, 2.84. Found: C., 70.44; H, 7.76; N, 2.84.

Later fractions from the chromatography yielded an additional 0.61 g of product, viz., 7-hydroxy-3-(4-hydroxy-4-phenylpiperidino)chromen-4-one, formed by desilylation during the reaction. This material is also useful as an intermediate in the preparation of products described below using like methods.

EXAMPLE 2 cis- and trans-3-(4-Hydroxy-4-phenylpiperidino)-7-(triisopropylsilyloxy)-4-chromanol Title product of the preceding Example (2.0 g, 4.1 mmol) was dissolved in ethanol (75 ml) and $NaBH_4$ (1.5 g, 39.7 mmol) was added all at once. This mixture was stirred overnight at ambient temperature. Additional $NaBH_4$ (0.75 g, 19.9 mmol) was added and, after stirring for an additional 5 hours, the reaction was quenched with excess water, concentrated, and the residue partitioned between ethyl acetate and water. The organic layer was washed with water and brine, dried over $CaSO_4$, and concentrated to give 1.7 g of light yellow solid, which was recrystallized from ether/hexanes to yield 1.0 g (50%) of cis-title product as a white solid; mp 145.5°–146.5° C. IR(KBr) 3380, 2940, 2860, 1615, 1280, 1173, 1040. Anal. calcd. for $C_{29}H_{43}NO_4Si$: C, 69.98; H, 8.71; N, 2.81. Found: C, 70.02; H, 8.58; N, 2.81.

Silica gel chromatography of the recrystallization filtrate, using gradient elution with ethyl acetate/hexanes, gave 70 mg additional cis-title product, followed by 0.27 g (14%) of yellow solid which was shown by NMR to be an 85:15 mixture of trans- and cis-title products. This mixture was used directly in the further synthesis of trans-product. $^{13}C$ NMR (trans) 156.7, 154.5, 148.2, 128.8, 128.4, 127.2, 124.5, 117.2, 113.4, 107.2, 71.4, 64.8, 64.1, 63.4, 48.4, 43.0, 39.0, 17.9, 12.7. HRMS Calcd. for $MH^+$, 498.3041; observed, 498.3011.

EXAMPLE 3 cis-3-(4-Hydroxy-4-phenylpiperidino)-4,7-chromandiol

To cis-title product of the preceding Example (0.94 g, 1.89 mmol) dissolved in THF was added 1M tetrabutylammonium fluoride in THF (1.95 ml, 1.95 mmol). The resulting solution was stirred at ambient temperature for 1.5 hours, then concentrated and chromatographed on silica gel, using gradient elution with ethyl acetate/hexanes, to give present title product (0.72 g), which was recrystallized from ethanol/ether to give 0.54 g (84%) of white solid; mp 171.5°–172.5° C. Anal. calcd. for $C_{20}H_{23}NO_4 \cdot 0.25\ H_2O$: C, 69.45; H, 6.84; N, 4.05. Found: C, 69.26; H, 6.79; N, 3.96.

EXAMPLE 4 trans-3-(4-Hydroxy-4-phenylpiperidino)-4,7-chromandiol

By the method of the preceding Example, the trans-title product of Example 2 (0.27 g, 0.54 mmol; containing 15% cis-isomer) was converted to crude, product (0.17 g) as an oily white solid which was recrystallized from ethanol to produce 57 mg (30%) of present title product as a white solid; mp 192.5°–193° C.; Anal. calcd. for $C_{20}H_{23}NO_4$: C, 70.36; H, 6.79; N, 4.10. Found: C, 70.06; H, 6.88; N, 4.04.

EXAMPLE 5

3-(4-Hydroxy-4-phenylpiperidino)-7-(triisopropylsilyloxy)-4-chromanone 7-(Triisopropylsilyloxy)-4-chromanone (2.0 g, 6.2 mmol) was dissolved in $CCl_4$ (45 ml). Bromine (0.3 ml, 6.4 mmol) in $CCl_4$ (5 ml) was added dropwise at ambient temperature over 10 minutes. The reaction initially turned dark red but after stirring for 10 minutes the color changed to light yellow. This yellow solution was washed with dilute $NaHSO_3$, saturated $NaHCO_3$ and brine, dried by filtering through phase separatory paper, and concentrated to yield a brown oil (2.3 g, 93%) which NMR showed was a 2.5:1:1 mixture of 3-bromo-7-(triisopropylsilyloxy)-4-chromanone, 3,3-dibromo-7-(triisopropylsilyloxy)-4-chromanone and starting material. This crude mixture (2.3 g, 5.6 mmol) was combined with 4-hydroxy-4-phenyl piperidine (1.0 g, 5.8 mmol), triethylamine (0.9 ml, 6.5 mmol) and ethanol (50 ml). The reaction was refluxed for 3 hours, then cooled and concentrated. The residue was partitioned between ethyl acetate and water. The organic layer was washed with water and brine, dried over $CaSO_4$, concentrated and the residue chromatographed on silica gel using gradient elution with ethyl acetate/hexanes to give 80 mg (3%) of present title product as a yellow solid, mp 132°–132.5° C.

EXAMPLE 6 cis-3-(4-Hydroxy-4-phenylpiperidino)-4,7-Chromandiol

Title product of the preceding Example (80 mg. 0.16 mmol) was dissolved in ethanol (10 ml) and NaBH$_4$ (7 mg, 0.2 mmol) added. The mixture was stirred at ambient temperature for 6 hours; then quenched with water and concentrated. The residue was partitioned between ethyl acetate and water, and the organic layer washed with water and brine, dried over CaSO$_4$ and concentrated to give the crude cis- product of Example 2 as a yellow oil (50 mg, 63%). This material was desilylated by the method of Example 3 to yield present title product (15 mg, 44%) identical with the product of Example 3.

EXAMPLES 7-13

By the method of Example 1, the following additional compounds were prepared from the appropriately substituted 3,3-dibromo-4-chromanone and the appropriately substituted piperidine derivative in the yield and having properties as indicated.

7. 3-(4-Benzyl-4-hydroxypiperidino)-7-(triisopropylsilyloxy)chromen-4-one; 34%; mp 115°-116° C. (from ether/hexanes).

8. 3-(4-Phenylpiperidino)-7-(triisopropylsilyloxy)-chromen-4-one; 46%; mp 99°-100° C. (from ether/hexanes).

9. 3-(4-Benzylpiperidino)-7-(triisopropylsilyloxy)-chromen-4-one; 38%; oil; $^{13}$C NMR 160.7, 157.2, 143.6, 140.5, 137.0, 129.2, 128.2, 127.6, 125.8, 118.4, 106.7, 50.7, 43.3, 37.8, 32.1, 17.8, 12.3.

10. 3-[4-Hydroxy-4-(2-phenylethyl)piperidino]-7-(triisopropylsilyloxy)chromen-4-one; 2%; oil; $^{13}$C NMR 174.7, 160.9, 157.4, 144.3, 142.3, 136.8, 128.5, 128.3, 127.6, 125.9, 118.7, 106.8, 69.5, 46.3, 45.0, 36.8, 29.3, 17.9, 12.7.

11. 6-Chloro-3-(4-hydroxy-4-phenylpiperidino)chromen-4-one; 40%; mp 191.5°-192° C. (from CHCl$_3$/ether).

12. 6-Fluoro-3-(4-hydroxy-4-phenylpiperidino)-chromen-4-one; 40%; mp 183.5°-184° C. (from CHCl$_3$/ether).

13. 3-(4-Hydroxy-4-phenylpiperidino)chromen-4-one; 85%; mp 168°-168.5° C. (from ethanol/ether).

EXAMPLES 14-20

By the method of Example 2, the following additional compounds were prepared from the products of Examples 7-13 in the yield and having properties as indicated.

14. cis-3-(4-Benzyl-4-hydroxypiperidino)-7-(triisopropylsilyloxy)-4-chromanol; 29%; mp 172.0°-172.5° C. (from ethanol/ether); and a 2:1 cis:trans-mixture of 3-(4-benzyl-4-hydroxypiperidino)-7-triisopropyloxy)-4-chromanol; 40%; suitable for separation into additional cis-isomer and the trans-isomer by further column chromatography.

15. cis-3-(4-Phenylpiperidino)-7-(triisopropylsilyloxy)-4-chromanol; 69%; mp 148°-148.5° C. (from ethanol/ether).

16. cis-3-(4-Benzylpiperidino)-7-(triisopropylsilyloxy)-4-chromanol; 55%; oil; $^{13}$C-NMR 157.2, 154.8, 140.4, 131.7, 129.1, 128.2, 125.9, 115.3, 113.4, 107.1, 62.3, 61.7, 60.8, 51.5, 49.3, 43.1, 37.8, 32.3, 32.2, 17.9, 12.7.

17. cis-3-[4-Hydroxy-4-(2-phenylethyl)piperidino]-7-(triisopropylsilyloxy)-4-chromanol; 25%; white solid.

18. cis-6-Chloro-3-(4-hydroxy-4-phenylpiperidino)-4-chromanol; 16%; mp 185°-185.5° C. (from ethanol/ether); and a 3:2 cis:trans mixture; 37%; suitable for separation by further chromatography.

19. cis-6-Fluoro-3-(4-hydroxy-4-phenylpiperidino)-4-chromanol; 26%; mp 189°-189.5° C. (from ethanol/ether); and a 2:1 cis:trans mixture; 28%; from which 80% pure trans-isomer was obtained by fractional crystallization from ethanol/ether, mp 164°-168° C., in 4% over-all yield.

20. cis-3-(4-Hydroxy-4-phenylpiperidino)-4-chromanol; 58%; mp 187.5°-188° C. (from ethanol/ether); and, from the crystallization mother liquor, a 1:3 cis:trans mixture; 3%; mp 170°-174° C.

EXAMPLES 21-24

By the method of Example 3, the following additional compounds were prepared from the products of Examples 7-10 in the yield and having properties indicated.

21. cis-3-(4-Benzyl-4-hydroxypiperidino)-4,7-chromandiol; 85%; mp 181°-182° C. (from ethanol/ether).

22. cis-3-(4-Phenylpiperidino)-4,7-chromandiol; 67%; mp 195.0°-195.5° C. (dec) (from ethanol/ether).

23. cis-3-(4-Benzylpiperidino)-4,7-chromandiol; 31%; mp 164.5-165.0 (from ethanol/ether).

24. cis-3-[4-Hydroxy-4-(2-phenylethyl)piperidino]-4,7-chromandiol; 54%; mp 97°-100° C.

EXAMPLE 25

2-(4-Hydroxy-4-phenylpiperidino)-6-methoxy-1-tetralone

Following the procedure of Example 1, title product was obtained from 2-bromo-6-methoxytetralone (2.8 g, 11.5 mmol), 4-hydroxy-4-phenylpiperidine (2.5 g, 14.1 mmol) and triethylamine (4.0 ml, 28.7 mmol) in acetonitrile (75 ml) with overnight stirring. The concentrated product was chromatographed on silica gel using ethyl acetate/hexanes gradient elution to yield 1.33 g (33%) of present title product; mp 149.5°-150.5° C. (from ethanol/ether).

EXAMPLE 26 cis- and trans-1,2,3,4-Tetrahydro-2-(4-hydroxy-4-phenylpiperidino)-6-methoxy-1-napthol By the method of Example 2, title product of the preceding Example (1.0 g, 2.85 mmol) was converted to present title products, separated by chromatography on silica gel (using gradient elution with ethyl acetate/hexanes) and recrystallization from ethanol/ether:

trans-isomer, 0.13 g (13%), more polar, mp 155°-155.5° C.

cis-isomer, 0.033 g (3%), less polar, 159°-160° C.

EXAMPLES 27-28

By the method of Example 25, appropriately substituted 2-bromo-1-tetralones were converted to the following additional compounds:

27. 2-(4-Hydroxy-4-phenylpiperidino)-1-tetralone; 21%; mp 148°-151° C. (dec.) (from ethanol/ether).

28. 2-(4-Hydroxy-4-phenylpiperidino)-6-(triisopropylsilyloxy)-1-tetralone; 36%; mp 151°-153° C. (from ethanol/ether).

EXAMPLE 29 trans-1,2,3,4-Tetrahydro-2-(4-hydroxy-4-phenyl-piperidino)-1-naphthol)

By the method of Example 26, the product of Example 27 was converted to present title product in 5% yield; mp 184°-184.5° C.

EXAMPLE 30 trans-1,2,3,4-Tetrahydro-2-(4-hydroxy-4-phenyl-piperidino)-6-(triisopropylsilyloxy)-1-naphthol The product of Example 28 (0.75 g, 1.61 mmol) in tetrahydrofuran (25 ml) was added dropwise over 10 minutes to a stirred slurry of LiAlH$_4$ (0.065 g, 1.71 mmol) in tetrahydrofuran (75 ml). The resulting gray-green mixture was stirred at ambient temperature for 30 minutes, then quenched with excess Na$_2$SO$_4$.10H$_2$O. After stirring for 15 minutes, the quenched reaction mixture was dried over Na$_2$SO$_4$, concentrated to a 0.65 g residue, and chromatographed on silica gel using gradient elution with ethyl acetate/hexanes to yield 0.45 g (60%) of present title product; mp 171.0°-171.5° C. (from ethanol/ether).

EXAMPLE 31 trans-1,2,3,4-Tetrahydro-2-(4-hydroxy-4-phenyl-piperidino)-1,6-naphalenediol

By the method of Example 3, the product of Example 30 (0.35 g, 0.75 mmol) was converted to 0.12 g (46%) of present title product; mp 181°-183° C. (from ethanol/ether); IR (KBr) 3380, 3230, 2950, 2850, 1610, 1495, 1240, 1110, 1045, 770, 705.

EXAMPLE 32

5-(Triisopropylsilyloxy)-2-(4-hydroxy-4-phenyl-piperidino)-1-indanone

By the method of Example 1, 2-bromo-5-(triisopropylsilyloxy)-1-indanone was converted to present title product in 41% yield as a foamy solid; $^{13}$C-NMR 203.3, 163.2, 154.9, 148.1, 129.8, 128.5, 128.4, 127.0, 125.9, 124.5, 120.5, 116.7, 71.0, 69.4, 46.2, 44.5, 42.0, 38.2, 37.3, 27.3, 18.0, 12.7.

EXAMPLE 33 cis- and trans-5-(Triisopropylsilyloxy)-2-(4-hydroxy-4-phenyl-piperidino)-1-indanol By the method of Example 2, title product of the preceding Example was converted to present title products which were separated by chromatography on silica gel using gradient elution with ethyl acetate/hexanes.

cis-isomer, 27% yield; mp 169.5°-170° C. (from ether/hexanes); IR (KBr) 3467, 2959, 2894, 2867, 1610, 1490, 1294, 1138, 964, 883, 698.

trans-isomer, 43% yield; mp 143°-144° C.; IR(KBr) 3321, 2945, 2867, 1613, 1490, 1465, 1291, 1265, 1135, 966, 702, 681.

EXAMPLES 34-35

By the method of Example 3, the title product of the preceding Example were converted to:

34. cis-2-(4-Hydroxy-4-phenylpiperidino)-1,5-indandiol; 54%; mp 212.5°-213.5° C.; $^{13}$C-NMR 157.7, 150.2, 143.3, 134.8, 127.9, 126.2, 126.1, 124.8, 113.5, 111.2, 71.5, 69.7, 69.6, 47.8, 47.1, 38.0, 37.9, 34.2.

35. trans-2-(4-Hydroxy-4-phenylpiperidino)-1,5-indandiol; 71%; mp 196.0°-197.0° C; $^{13}$C-NMR 157.1, 150.3, 140.8, 135.6, 127.8, 126.1, 124.9, 124.8, 113.8, 110.7, 76.7, 75.2, 69.7, 47.3, 38.1, 33.9.

PREPARATION 1

7-(Triisopropylsilyloxy)-4-chromanone

7-Hydroxy-4-chromanone (1.2 g, 7.3 mmol; Dann et al., Ann. 587, 16, 1954) and imidazole (1.0 g, 14.7 mmol) were dissolved in DMF (10 ml). Triisopropylsilyl chloride (1.8 ml, 8.2 mmol) in DMF (2 ml) was added dropwise at ambient temperature over 10 minutes. After stirring for 3 hours, the mixture was poured onto 100 ml ice and water, and extracted with ether (2×100 ml). The combined ether extracts were washed with 1M LiCl and then brine, dried over CaSO$_4$, and concentrated to a brown oil which was purified by Kugelrohr distillation (0.5 torr, 70°-90° C.). This removed a colorless, viscous oil impurity and left the brown oil product in the distillation pot (2.0 g, 85%). IR (KBr) 2945, 2867, 1685, 1605, 1268, 1163. HRMS Calcd. for MH$^+$, 320.1807; observed, 320.1842.

PREPARATION 2

3,3-Dibromo-7-(triisopropylsilyloxy)-4-chromanone

Title product of the preceding Preparation (7.1 g, 22.1 mmol) was dissolved in carbon tetrachloride (170 ml). Bromine (2.5 ml, 48.5 mmol) in CCl$_4$ (30 ml) was added dropwise at ambient temperature over 20 minutes. The reaction was stirred for 0.5 hour to give a dark red solution, which was then washed in sequence with dilute NaHSO$_3$ (100 ml), saturated NaHCO$_3$ (2×75 ml) and brine (100 ml), dried by filtering through phase separating paper, and concentrated to leave a dark orange oil (9.9 g, 94%). $^{13}$C-NMR 179.0, 164.3, 161.9, 131.3, 116.6, 109.9, 107.5, 78.0, 60.9, 17.8, 12.7. HRMS Calcd. for MH$^+$, 479.0076; observed, 479.0066.

PREPARATIONS 3-5

By the method of the preceding Preparation, the following additional compounds were prepared from the suitably substituted 4-chromanone.

3. 3,3-Dibromo-6-chloro-4-chromanone; 64%; mp 128°-129° C. (from ethanol/ether); IR (KBr) 3060, 2930, 1710, 1475, 1137, 838.

4. 3,3-Dibromo-6-fluoro-4-chromanone; 70%; mp 90°-91° C. (from ether/hexanes); IR (KBr) 3380, 3080, 1720, 1705, 1690, 1485, 1275, 1235, 1170, 1127, 850, 727.

5. 3,3-Dibromo-4-chromanone; 90%; mp 67°-68° C. (from ether/hexanes); IR (KBr) 3380, 1705, 1610, 1480, 1463, 1300, 818.

PREPARATION 6

2-Bromo-6-methoxytetralone

6-Methoxytetralone (2.0 g, 11.4 mmol) and bromine (0.6 ml, 11.7 mmol) were refluxed in ether (50 ml) for 30 minutes. The reaction mixture was cooled, concentrated, the residue partitioned between ethyl acetate and dilute NaHSO$_3$. The organic layer was washed with saturated NaHCO$_3$ and water, dried over CaSO$_4$, and concentrated to an oil (2.83 g, 100%); $^1$H-NMR 8.03 (d, J=9.0 Hz, 1H), 6.84 (dd, J$_1$=9.0 Hz, J$_2$=2.7 Hz, 1H), 6.69 (d, J=2.3 Hz, 1H), 4.66 (t, J=4.1 Hz, 1H), 3.84 (s,3H), 3.20-3.30 (m, 1H), 2.82-2.90 (m, 1H), 2.34-2.50 (m, 2H).

PREPARATION 7

2-Bromotetralone

By the method of the preceding Preparation, tetralone (2.0 g, 13.7 mmol) was converted to present title product (2.7 g, 87%) as an oil. $^1$H-NMR 8.08 (d, J=7.9 Hz, 1H), 7.51 (t, J=7.5 Hz, 1H), 7.23–7.36 (m, 2H), 4.72 (t, J=4.2 Hz, 1H), 3.25–3.36 (m, 1H), 2.92–2.97 (m, 1H), 2.40–2.58 (m, 2H).

PREPARATION 8

1-(Benzyloxycarbonyl)-4-hydroxy-4-(2-phenylethyl)-piperidine

Magnesium turnings (1.7 g, 70.0 mmol) were slurried in ether (10 ml) and a solution of (2-bromoethyl)benzene (11.8 g, 63.8 mmol) in ether (15 ml) was added dropwise, slowly at first, until the reaction had initiated and then more rapidly to maintain heat generation. After heating overnight at 60° C., the reaction was cooled to 0° C., diluted with ether (200 ml), and piperidone benzylcarbamate (14.9 g, 63.9 mmol) in ether (100 ml) was added dropwise. A white precipitate formed and the mixture was stirred vigorously at room temperature for 8 hours, then quenched with water and stirred for 1 hour longer. The aqueous layer was separated and extracted with ethyl acetate (3×100 ml). The organic layers were combined, washed with brine, dried over CaSO$_4$, and concentrated to give a clear oil. Purified title product was obtained by chromatography on silica gel (25% ethyl acetate/hexanes) as a clear oil (9.2 g, 43%): IR (CHCl$_3$) 3585, 2939, 1692, 1470, 1429, 1363, 1311, 1275, 1260, 1190.

PREPARATION 9

4-Hydroxy-4-(2-phenylethyl)piperidine

Under N$_2$, title product of the preceding Example (8.71 g, 25.66 mmol) was dissolved in ethanol (250 ml), 10% palladium on carbon (936 mg) was added and the mixture hydrogenated in Parr apparatus at 45–50 psig for 16 hours. Catalyst was recovered by filtration over diatomaceous earth, and the mother liquor concentrated to give present title product as a yellow, oily solid, 4.96 g (99%); IR (CHCl$_3$) 3539, 2930, 1715, 1620, 1600, 1452, 1372, 1351, 1322, 1042.

PREPARATION 10

6-(Triisopropylsilyloxy)-1-tetralone

By the method of Preparation 1, 6-hydroxy-1-tetralone (5.0 g, 30.83 mmol; Durden, J. Agr. Food Chem., v. 19, p. 432, 1971) was converted to present title product as an oil purified by Kugelrohr distillation, 8.3 g (85%); IR (CHCl$_3$) 2937, 2889, 2862, 1666, 1593, 1349, 1333, 1319, 1274, 1226, 1109, 969, 898.

PREPARATION 11

2-Bromo-7-(triisopropylsilyloxy)-1-tetralone

By the method of Preparation 6, title product of the preceding Preparation (8.3 g, 26.1 mmol) was converted to present title product, 9.7 g (94%), which, by $^1$H-NMR, also contained some of the corresponding 2,2-dibromo derivative. This product was used without purification in the next step.

PREPARATION 12

5-(Triisopropylsilyloxy)-1-indanone

By the method of Preparation 1, 5-hydroxy-1-indanone was converted to present title product in quantitative yield; mp 63.0°–63.5° C.

PREPARATION 13

2-Bromo-5-(triisopropylsilyloxy)-1-indanone

By the method of Preparation 6, title product of the preceding Preparation was converted to present title product, contaminated with the corresponding dibromo product, in quantitative yield; $^1$H-NMR 7.72 (d, H), 6.89 (dd, 1H), 6.83 (m, 1H), 4.62 (dd, 1H), 3.74 (dd, 1H), 3.34 (dd, 1H), 1.22–1.34 (m, 3H), 1.10 (d, 18H). Without purification, this product was used directly in the next step (Example 32, above).

I claim:

1. A compound having the formula

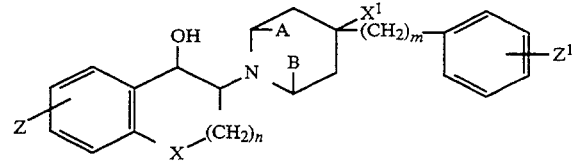

wherein

A and B are taken together and are —CH$_2$CH$_2$— or A and B are taken separately and are each H;

X is CH$_2$ or O;

X$^1$ is H or OH;

Z is H, F, Cl, Br or OH;

Z$^1$ is H, F, Cl, Br or (C$_1$–C$_3$)alkyl;

n is 0 or 1; and m is 0 or an integer from 1 to 6; or a pharmaceutically acceptable salt thereof.

2. A compound of claim 1 wherein A and B are taken separately; Z is H, F, Cl or OH; Z$^1$ is H; and m is 0, 1 or 2.

3. A compound of claim 2 wherein X is O and n is 1 having the cis relative stereochemical formula

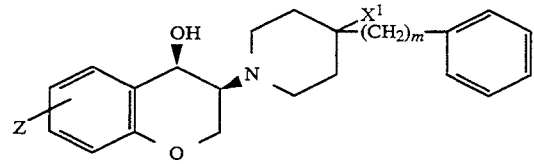

4. A compound of claim 3 wherein Z is substituted at the 7-position of the chroman ring system, and is OH.

5. The compound of claim 4 wherein X$^1$ is OH and m is 0.

6. The compound of claim 4 wherein X$^1$ is OH and m is 2.

7. The compound of claim 4 wherein X$^1$ is H and m is 0.

8. The compound of claim 4 wherein X$^1$ is H and m is 1.

9. A compound of claim 1 wherein X is CH$_2$ and n is 1 having the trans relative stereochemical formula

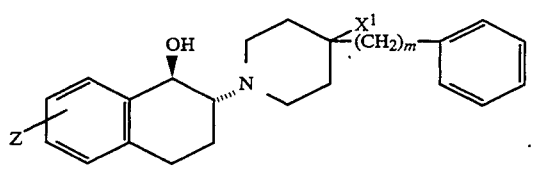

10. A compound of claim 9 wherein Z is substituted at the 6-position of the tetrahydronaphthalene ring system, and is OH.

11. The compound of 10 wherein $X^1$ is OH and m is 0.

12. A compound of claim 2 wherein X is $CH_2$ and n is 0.

13. A compound of claim 12 wherein Z and $X^1$ are each OH and m is 0 having the formula

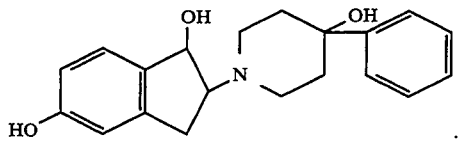

14. The compound of claim 13 having the relative stereochemical formula

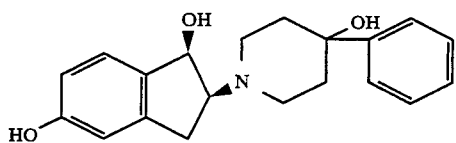

15. The compound of claim 13 having the relative stereochemical formula

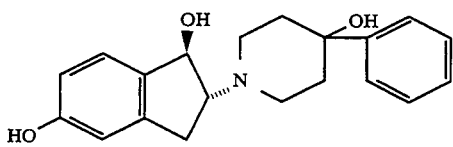

16. A pharmaceutical composition comprising a neuroprotective amount of a compound of claim 1 and a pharmaceutically acceptable carrier.

17. A pharmaceutical composition comprising a neuroprotective amount of a compound of claim 2 and a pharmaceutically acceptable carrier.

* * * * *